United States Patent [19]
Pohlig

[11] Patent Number: 5,507,836
[45] Date of Patent: Apr. 16, 1996

[54] ADJUSTABLE THIGH PROSTHESIS FOR COMPENSATION OF VOLUME VARIATIONS AND IMPOSING FEMUR ADDUCTION

[76] Inventor: Kurt Pohlig, Ludwigstrasse 18/20, D-8220 Traunstein, Germany

[21] Appl. No.: 133,177
[22] PCT Filed: Feb. 11, 1993
[86] PCT No.: PCT/EP93/00332
  § 371 Date: Oct. 14, 1993
  § 102(e) Date: Oct. 14, 1993
[87] PCT Pub. No.: WO93/15695
  PCT Pub. Date: Aug. 19, 1993

[30] Foreign Application Priority Data
Feb. 14, 1992 [JP] Japan ............... 42 04 482.0

[51] Int. Cl.[6] ........................... A61F 2/80
[52] U.S. Cl. ................ 623/37; 623/36; 623/33
[58] Field of Search ....................... 623/32–37

[56] References Cited

U.S. PATENT DOCUMENTS

| | | | |
|---|---|---|---|
| 1,893,853 | 1/1933 | Tullis | 623/37 |
| 2,500,622 | 3/1950 | Aho | 623/36 |
| 3,671,980 | 6/1972 | Baird | 623/37 |
| 4,300,245 | 11/1981 | Saunders | 623/35 |
| 4,923,475 | 5/1990 | Gosthnian et al. | 623/37 |
| 5,108,456 | 4/1992 | Coonan | 623/37 |
| 5,139,523 | 8/1992 | Paton et al. | 623/37 |
| 5,246,464 | 9/1993 | Sabolich | 623/33 |
| 5,314,497 | 5/1994 | Fay et al. | 623/34 |

FOREIGN PATENT DOCUMENTS

| | | | |
|---|---|---|---|
| 0019612 | 5/1980 | European Pat. Off. | 623/37 |
| 0151834 | 8/1985 | European Pat. Off. | 623/27 |
| 1548465 | 12/1965 | France | 623/37 |
| 2420335 | 10/1979 | France | 623/37 |
| 2540138 | 3/1977 | Germany | 623/37 |
| 8707615 | 9/1987 | Germany . | |

Primary Examiner—David H. Willse
Attorney, Agent, or Firm—Gardner, Carton & Douglas

[57] ABSTRACT

A thigh prosthesis with a shell-type sleeve and a plurality of cheeks adjustable sleeve-inward and sleeve-outward arranged on the sleeve wall, is characterized in that such cheeks are elongated and are disposed in the dorso-lateral zone in connection to the side of the thigh bone, extending from proximal to distal, and in approximately round form in the medial distal zone. The stump zones concerned have proved especially well suited for the initiation of lateral forces and for volume reductions possibly sought or to be compensated therewith on the stump. Moreover, by abduction, the abnormal position of the thigh bone frequently encountered in thigh-amputated patients can be corrected. Preferably the cheeks are formed by inflatable cushions which, in the case of two-sleeve prostheses, are advantageously arranged between an outer sleeve and an inner sleeve. A further such cushion may be disposed within the sleeve in the stump end zone.

10 Claims, 4 Drawing Sheets

ADJUSTABLE THIGH PROSTHESIS FOR COMPENSATION OF VOLUME VARIATIONS AND IMPOSING FEMUR ADDUCTION

The present invention relates to a thigh prosthesis that ensures good surface adhesion of the prosthesis to an amputee's stump and adduction of the femur.

BACKGROUND OF THE INVENTION

In such prostheses it is generally endeavored to fit the sleeve as precisely as possible to the contours of the limb stump, in order to achieve, besides a firm seating of the prosthesis, as broad as possible a distribution of pressure upon the surface area. Recent developments have provided that the sleeve, as a result of "pumping" in the walking process there occurs a subpressure, whereby the sleeve, possibly even without additional aids, is held onto the stump. Studies have concluded that, assuming a prosthesis sleeve is well fitted in such manner, in the stump there takes place to a certain degree a hydrostatic pressure compensation. On the other hand, however, it has also been found that not all areas of the stump are equally suited for the pressure absorption, but rather, in principle, besides some zones that are more pressure-sensitive, there are other zones that are better suited to absorb external pressure. It has been ascertained that volume changes of the stump occur more noticeably in certain areas than in others. Such volume changes may occur in the short term, for example, through temperature differences and metabolically conditioned swellings or contractions depending upon, among other things, the time of day, or may occur in the longer term through weight gain or loss of the patient, muscular atrophy or the like. While attempts have been made to compensate for the differing pressure absorption capacities of the different areas of the stump by providing an attachment sleeve that is contoured, such as a design which includes an inner sleeve that fits within an outer sleeve, such a design has inherent deficiencies. Furthermore, it is difficult to attach such a conventional prosthesis for a limb which requires a narrow sleeve. For such a prosthesis, there is a relatively conventional procedure where a stocking is placed over the stump and the loose end of the stocking is drawn out through a closable opening at the end of the sleeve. Then the stocking is removed through the opening of the sleeve until finally only the stump remains in the sleeve. As should be evident, this process is difficult in the case of a narrow sleeve.

U.S. Pat. Nos. 1,893,853 and 2,634,424, and German patent DE-GM 1,810,432 disclose devices and techniques for providing an attachment sleeve that fits the changing stump contour and to provide a more comfortable prosthesis for the wearer, by including in the attachment sleeve a cushion that is inflatable with a valve. Such prior art devices, however, are directed to a uniformly inflatable cushion, even if partially subdivided, which completely surrounds and is cohesive with the stump. German patent DE-GM 1,882,630 is directed to a similar device which, in order to reduce rocking of the stump with respect to the air cushion, provides an inlay of porous plastic material inside the air cushion.

The present invention is therefore directed to providing a thigh prosthesis which readily compensates for volume changes of the stump by the exertion of pressure in the form or manner of a correction pad. In the case of thigh amputations, the stump is much shorter and the thigh bone (femur) tends assume inside the stump an unnatural, so-called abduction position (a position spread outward), whereby the muscular bias tension required for the stabilization of the pelvis is reduced on the outside of the stump.

The foregoing problem is solved by the characterizing features of the claimed invention. The claimed invention is also directed to additional advantageous features and alternative embodiments thereof.

In accordance with the invention, the particular placement of the inflatable cushions make it possible for the prosthesis to compensate for changes of the stump volume in a very compatible manner. In accordance with another aspect of the invention, there is provided a means to correct the false or misplaced position of the femur in the form of another inflatable cushion disposed in the dorsolateral zone which provides a relative adduction position (a spread position, i.e., a position appearing swung toward the plane of symmetry of the body). Further, the invention makes it possible even to introduce into the thigh prosthetics a certain degree of prepackaging, since the invention may be adapted to fit with a relatively extensive variety and shapes of individual stumps. The prior art, in GB-PS 269,606 and DE-PS 742,945, discloses a relatively extended, mechanically spring-loaded cheek inside a leg prosthesis shell which is adjustable by means of screws.

The cheek features of the invention also have special importance since they make it possible, in combination with the good surface adhesion of the sleeve to the stump to provide a unique stump end contact, a feature which is extremely desirable from an orthopedic as well as from a general medical point of view. In addition, in accordance with the invention, it is possible to prevent an excessively sensitive narrowing of the stump in the circumferential zone with compression manifestations conditioned thereby and, furthermore, to introduce a substantial part of the prosthesis supporting force in a quite natural manner over the femur into the hip joint.

The arrangement of an inflatable cushion in the stump end region beside an annular one in the circumferential zone is known in principle from EP-OS 0 151 834 which is directed to a foldable lower-leg prosthesis for occasional use, for example in shower stalls. That prosthesis, however, presents no prosthesis sleeve which is even half-way adapted to the stump form.

With respect to the features inflatable cushion of the invention claimed, it should be noted that those features are, taken only by themselves, partly disclosed in U.S. Pat. No. 3,671,980 and Austrian Patent No. 364,073 relating to the fixing of a lower-leg prosthesis by means of one or more inflatable tori over the knee of the prosthesis wearer.

In the following some embodiments of the invention are described in more detail in conjunction with the drawings, in which.

Figure 1:
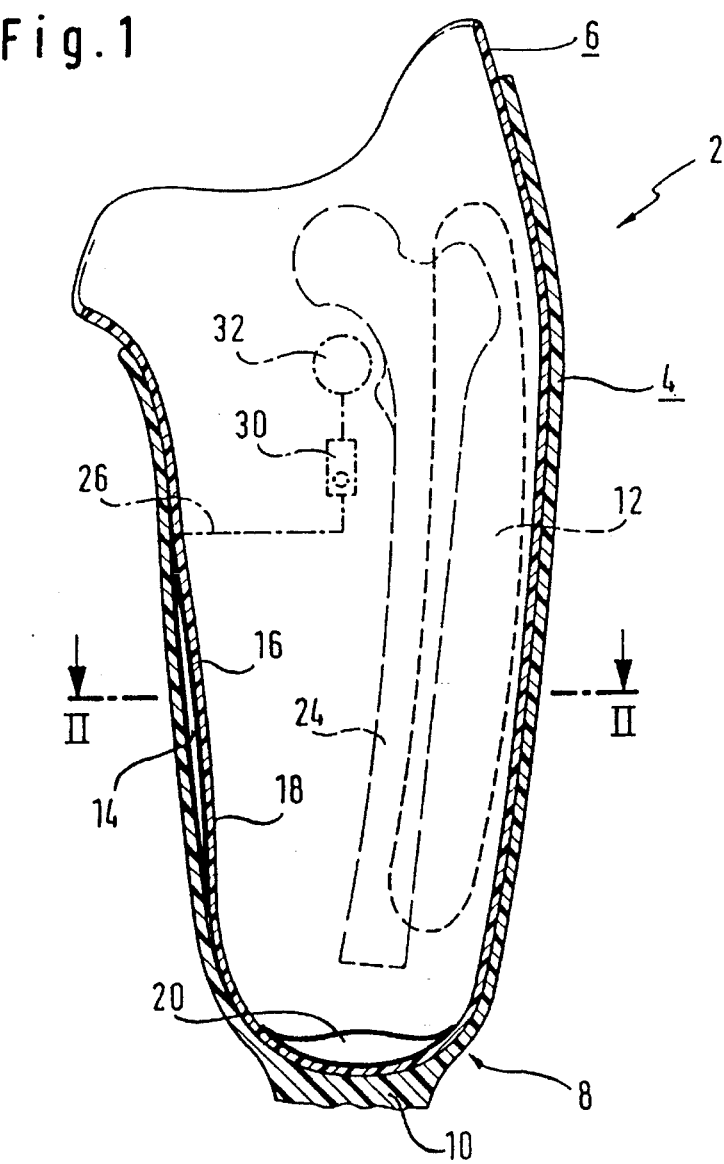
FIG. 1 shows, somewhat schematized, a longitudinal section through the sleeve of a thigh prosthesis in accordance with the invention.
Figure 2:
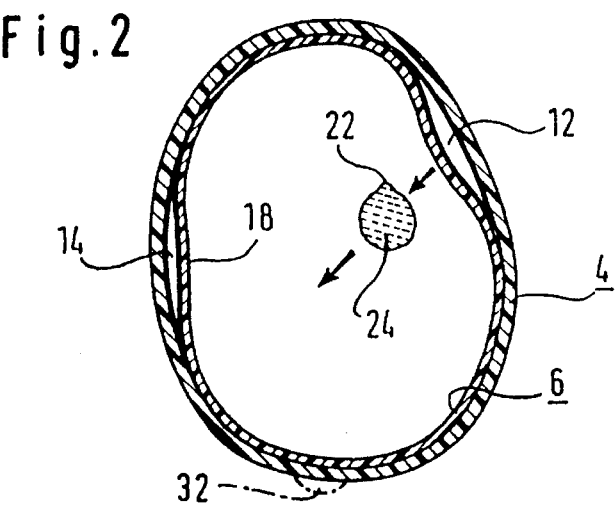
FIG. 2 shows a cross section through the plane of the line II—II of FIG. 1.

The thigh prosthesis 2 illustrated in part in FIGS. 1 and 2 includes a somewhat conventional shell-type outer sleeve 4 which is relatively stiff through reinforcements (not shown) or the like, and a relatively flexible inner sleeve 6 removably inserted within, which is adapted individually to the particular stump. Upon the closed distal end 8 of the outer sleeve 4 there is a column-type element 10 leading to the knee joint (sheathing is not shown in the drawing).

In deviation from conventional prostheses of this type, as illustrated there are arranged between the longitudinally running walls of the outer sleeve 4 and the inner sleeve 6 two discrete inflatable cushions 12 and 14, which with their inside-lying wall form cheeks, such as for example 16, by which the wall 18 of the inner sleeve 6 may be urged inward in certain areas, thereby achieving a local reduction of the sleeve volume. Another inflatable cushion, 20, is disposed inside of and at the distal end of the inner sleeve 6, where the wall 18 of the inner sleeve is not as flexible because of the two-dimensional and moreover stronger curvature.

More precisely stated, the cushions 12 and 14 are arranged in the dorso-lateral zone in relation to the side 22 of the thigh bone (femur) 24 (illustrated in broken lines) or in the medial distal zone. The cushion 12 extends from the proximal end to the distal end and has an elongated form, while the cushion 14 has a relatively round form.

Figure 3:
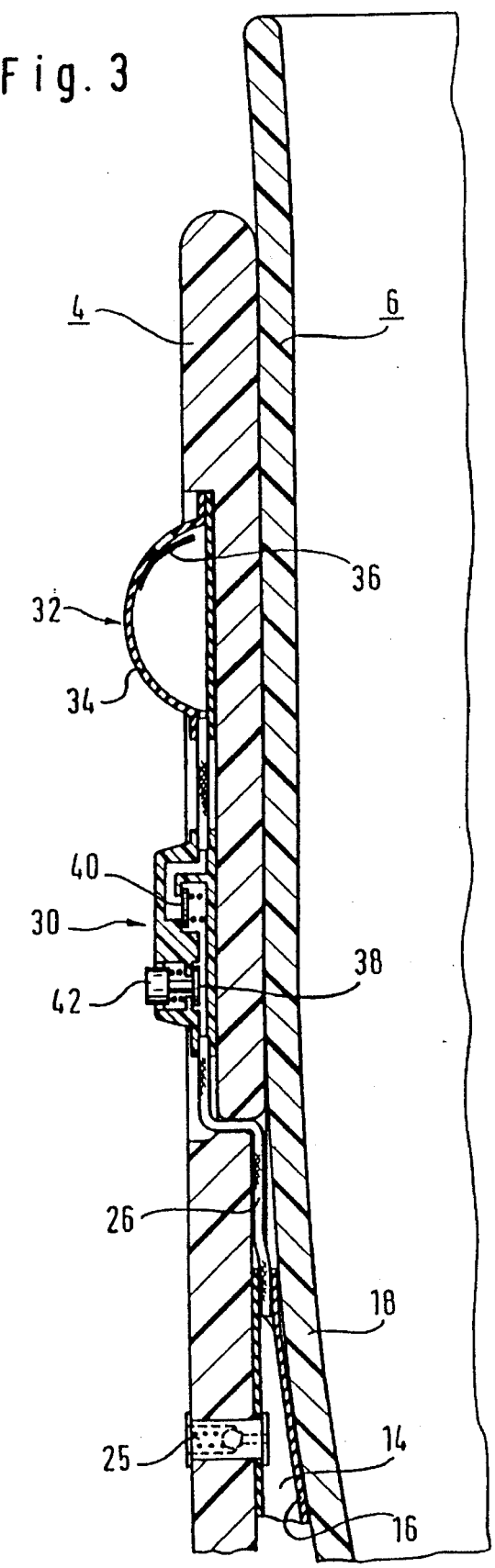
FIG. 3 is an enlarged and more detailed representation of some of the features of the invention illustrated in FIG. 1.

As indicated by the arrows in FIG. 2, the thigh bone 24 advantageously undergoes through the cushion 12 a relatively strong adduction, where, as previously stated, the abduction otherwise in thigh-amputees is usually correctable. The cushions 12 and 14 make it possible to reduce the sleeve volume and to convey to the stump in the sleeve, more precisely, in the inner sleeve 6, an increased surface adhesion. This surface adhesion, in turn, makes it possible, with the aid of the cushion 20, to create stump end contact with a precisely determinable stump end load or to increase the stump end load in the most desirable manner. In this regard, there can be provided, if so desired, a pressure-limiting valve, such as is illustrated in FIG. 3, on the cushion 14 as excess-pressure valve 25. Otherwise, however, the cushions make it possible to construct the inner sleeve 6 so that drawing-on of the prosthesis is substantially facilitated by deflating and thereby reducing the volume of the cushions.

As indicated in FIG. 1 and more evidently from FIG. 3, from the particular cushion, such as, for example, 14 a fine tube 26 leads to a valve 30, mounted on the prosthesis 2 to which there is connected a small manually actuatable air pump 32, such as is known in principle, for example, from perfume atomizers. In the example shown, the air pump 32 consists essentially of a flat rubber bulb which expands by tension, on which there is arranged a flap-type valve 36 which serves as an air intake valve. The air pump 32 may be worn inconspicuously under the clothing and is operable by repeated squeezing and relaxing of the rubber bulb 34. Air from atmosphere, which is drawn into the valve 36, can be forced through the valve 30 into the cushion 14, in order to inflate the cushion 14. The valve 30, a two way valve, is equipped with two valve members 38 and 40, one of which, 38, may be operated from outside by a push button 42, which is likewise operable through the clothing, which may be brought into its release position in order to ventilate the cushion 14 to the atmosphere. If so desired, also the aforementioned pressure limiting valve, such as, say, 25, may be integrated into the valve 30.

Figure 4:
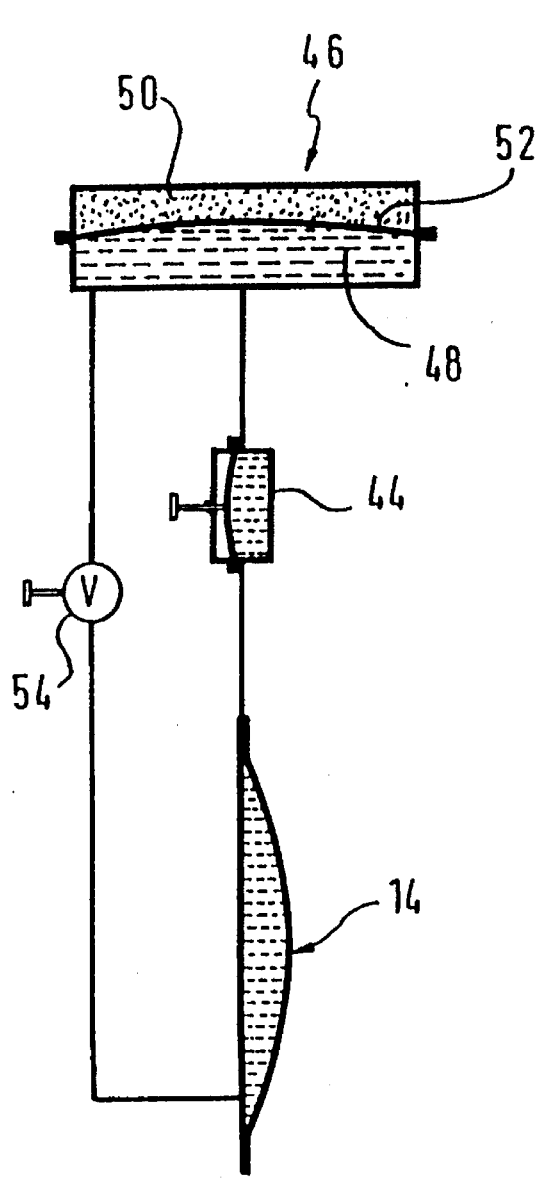
FIG. 4 illustrates schematically another embodiment of the invention.

FIG. 4 shows, purely schematically, an alternative embodiment in which valve 30 and air pump 32 from FIGS. 1 and 3 are replaced with a diaphragm pump 44 which is connected to a supply container 46; from the supply container a fluid 48 may be pumped into, for example, cushion 14. For this purpose the fluid 48 in the supply container 46 is pressurized by a gas cushion 50, which may be separated from the fluid 48 by a membrane 52. A manually actuatable reflex valve 54 makes it possible to empty the cushion 14 back into the supply container 46. The pressure necessary for this on the cushion 14 can be provided by the stump, for example, by lateral tilting of the prosthesis. Otherwise, it is also possible to provide a second diaphragm pump or the like for the emptying the cushion. The supply container 46 could also be similarly constructed as a cushion, out of which by manual pressure the fluid 48 may be displaced into the cushion 14 as well as conversely.

Where, as illustrated in FIGS. 1 and 2, within a prosthesis several cushions, as for example, the cushions 12, 14 and 20 are provided, these can, of course, be connected over a corresponding number of valves, such as, for example, 30 or 54, with a single supply container.

Figure 5:
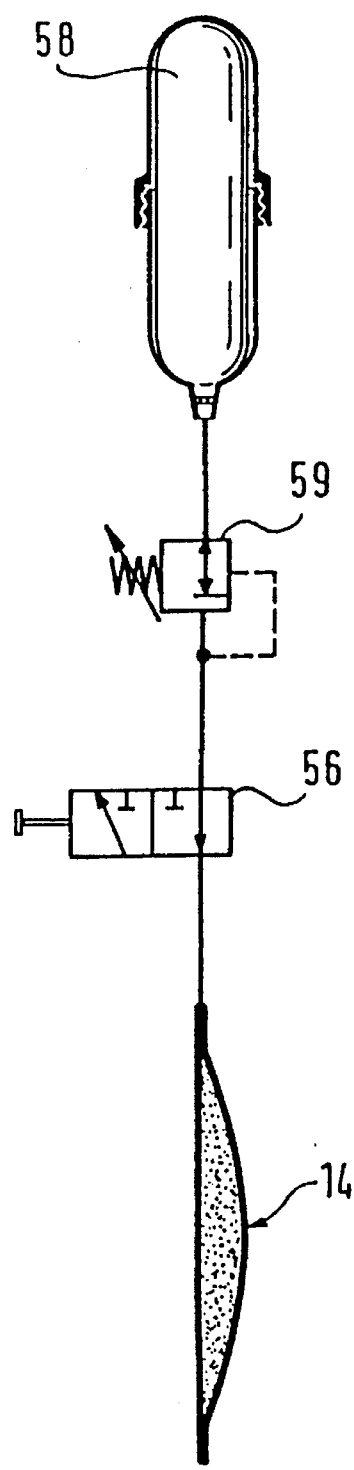
FIG. 5 illustrates yet another embodiment of the invention.

Instead of the manually operable pumps, such as, for example, 32 and 44, if so desired, of course, there may be provided an electrically operable pump, for example, a pump powered by a portable battery. Finally, however, each of the cushions, such as, for example, 12, 14 and 20 as illustrated in FIG. 5, may also be inflated or vented to atmosphere without pumps, as through a manually operable two-way valve 56 with a gaseous medium, preferably air, supplied from a pressurized supply container 58. As shown, the supply container 58 may be constructed as a changeable cartridge or tank. Between supply container 58 and two-way valve 56 there is provided a pressure-limiting valve in the form of a pressure-decreasing valve or reducing valve 59.

Figure 6:
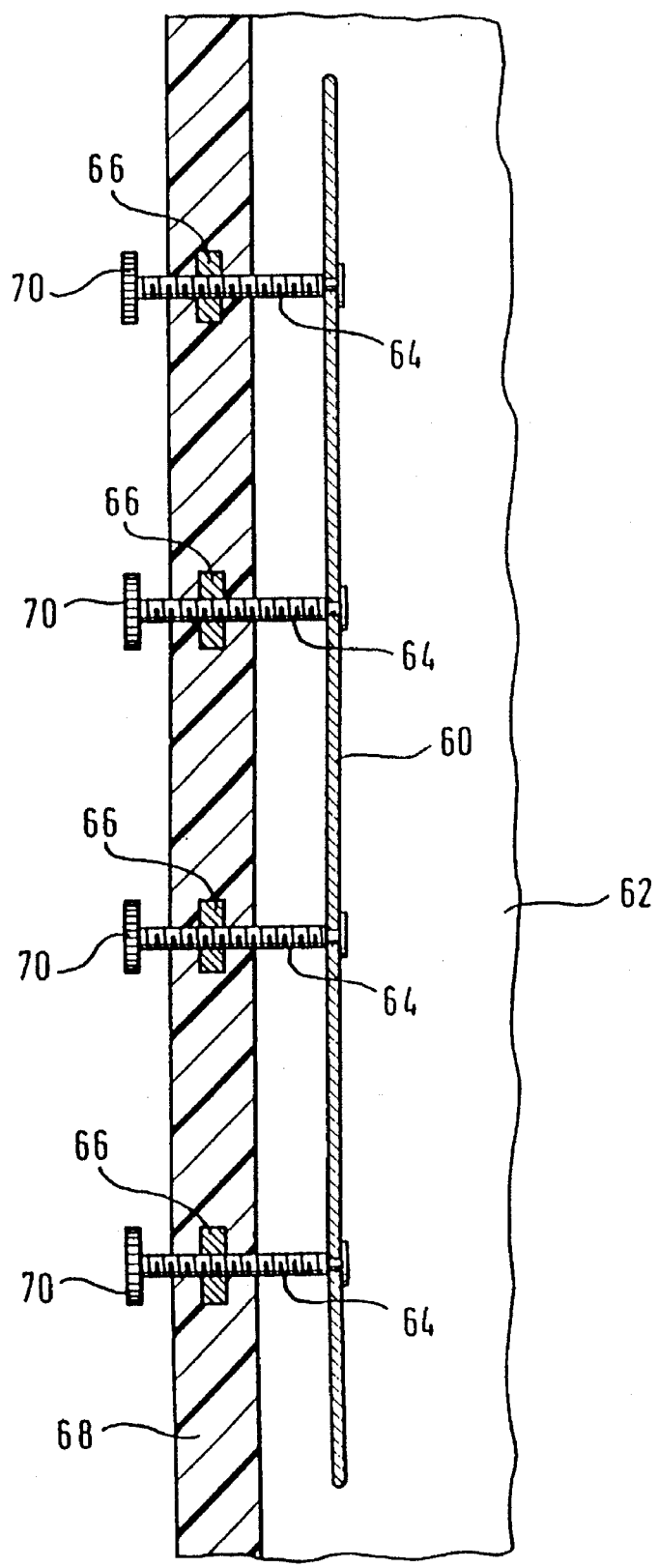
FIG. 6 illustrates in detail a longitudinal section of an alternative embodiment of the invention which is constructed without an inner sleeve.

FIG. 6, finally, illustrates yet another entirely different embodiment of the invention, in which the cheeks provided according to the invention are constructed as mechanically held and adjustable cheeks. More precisely stated, such a cheek, as illustrated, consists of a spring metal plate 60 which is held and supported in the interior of the sleeve 62 of the prosthesis, in this case a one-part sleeve, by means of several screws 64. The screws 64 are adjustably anchored in the spring metal plate 60 and threaded through nuts 66 which are held in the wall 68 of the sleeve 62. For their individual adjustment, the screws 64 provided with knurled heads 70 which are disposed on the outside of the wall.

Such a feature, by its nature, would most practically be implemented in the lateral wall of the prosthesis sleeve.

What is claimed is:

1. A thigh prosthesis comprising a shell-type sleeve, having an inner wall, a proximal open end, a distal stump end and a plurality of cheeks, substantially adjacent to the wall of the sleeve, said cheeks being adapted to be adjusted inwardly and outwardly, characterized in that one of said cheeks is of oblong shape and positioned to extend longitudinally from proximal to distal in the dorso-lateral region to be disposed next to the edge of the thigh bone, and another one of said cheeks which is approximately round in shape is disposed in the medial-distal region.

2. A thigh prosthesis according to claim 1, characterized in that an additional cheek is disposed in the stump end region.

3. A thigh prosthesis according to claim 2, characterized in that the sleeve is substantially closed in the stump end region and said cheek in the stump end region is formed by an inward wall of an inflatable cushion which rests on the bottom of said sleeve.

4. A thigh prosthesis according to claim 3, characterized in that the sleeve is comprised of an outer sleeve portion and an inner sleeve portion, the inner sleeve portion being designed to closely follow the contour of the stump, and further characterized in that the cushion which rests on the bottom of the sleeve is disposed inside of said inner sleeve portion.

5. A thigh prosthesis according to claim 1, characterized in that at least one of the cheeks is adjustable by means of one or more adjustment screws.

6. A thigh prosthesis according to claim 1, characterized in that at least one of said cheeks is formed by an inward wall of an inflatable cushion disposed inside of said sleeve and supported by an inner wall of said sleeve.

7. A thigh prosthesis according to claim 6, characterized in that said inflatable cushion includes a valve means for inflating said inflatable cushion.

8. A thigh prosthesis according to claim 6, characterized in that said cushion is arranged to be filled with a fluid from a fluid supply container.

9. A thigh prosthesis according to claim 6, characterized in that said cushion communicates with a pressure limiting valve.

10. A thigh prosthesis according to claim 1, characterized in that the sleeve is comprised of an outer sleeve portion and an inner sleeve portion wherein at least the circumferential area of said inner sleeve portion is flexible, and further characterized in that at least one of said cheeks is formed by an inward wall of an inflatable cushion disposed between said outer sleeve portion and said flexible area of said inner sleeve portion.

* * * * *